United States Patent [19]

Vandenberg et al.

[11] Patent Number: 4,933,872
[45] Date of Patent: Jun. 12, 1990

[54] METHOD AND SYSTEM FOR WAVEFRONT RECONSTRUCTION

[75] Inventors: Donald E. Vandenberg, Brockport, N.Y.; John C. Weaver, Bellerica, Mass.; Harold J. Liff; Thomas C. Antognini, both of Lexington, Mass.

[73] Assignee: Eastman Kodak Company, Rochester, N.Y.

[21] Appl. No.: 271,802

[22] Filed: Nov. 15, 1988

[51] Int. Cl.$^5$ .......................... G01J 1/20; G05B 13/00
[52] U.S. Cl. .................................. 364/513; 356/121; 382/15; 382/14; 250/208.1
[58] Field of Search ................ 364/513; 356/121, 354; 250/201, 553, 578; 382/14, 15, 29

[56] References Cited

U.S. PATENT DOCUMENTS

| | | | |
|---|---|---|---|
| H615 | 4/1989 | Feinleib et al. | 250/201 |
| 4,344,707 | 8/1982 | Massie | 356/354 |
| 4,490,039 | 12/1984 | Bruckler et al. | 356/121 |
| 4,666,298 | 5/1987 | Protz | 356/121 |

Primary Examiner—Jerry Smith
Assistant Examiner—Paul Gordon
Attorney, Agent, or Firm—Stephen C. Kaufman

[57] ABSTRACT

Method and system for wavefront reconstruction from an image plane intensity distribution profile. An imaging device may be an agent for producing the image plane intensity distribution profile, for example, a point spread function. In one embodiment, the method and system include defining a feature vector from the point spread function, and employing an adaptive computational architecture for associating the feature vector with at least one identifying characteristic of the imaging device, e.g., such as an amount of astigmatism.

23 Claims, 2 Drawing Sheets

METHOD AND SYSTEM FOR WAVEFRONT RECONSTRUCTION

BACKGROUND OF THE INVENTION

1. Field Of The Invention

This invention relates to radiation systems comprising a source of radiation and an imaging device.

2. Introduction To The Invention

Radiation systems comprising a source of radiation and an imaging device can cooperate so that the imaging device functions to produce a radiation field or radiation wavefront function at an image plane, for example, a focal plane. In particular, the source of radiation may be a microwave source, or an optical monochromatic point source, and the imaging device for the latter may be a mirror, a lens or a grating. The imaged radiation wavefront function produced by the imaging device at a selected image plane can provide a measure of the response of the system, i.e., the wavefront function includes the amplitude and the phase distribution of the radiation field as it is transformed by the imaging device.

SUMMARY OF THE INVENTION

For the radiation system just described, and under appropriate and ideal circumstances, the wavefront emerging from the imaging device at an entrance pupil is spherical. For real or practical radiation systems, in sharp contrast, the wavefront emerging from the imaging device at the entrance pupil is not spherical, but may contain "aberrations" which generally degrade the image quality at the image plane. These aberrations can be described quantitatively in terms of radiation phase variations over the entrance pupil, and include, e.g., the well-known monochromatic aberrations such as spherical aberration, coma, or astigmatism.

We are working on the critical problem of determining whether or not the imaging device (or other system component or media) may have introduced an unknown aberration into the radiation field. Further, we want to be able to specify what the aberration is, and how much the aberration is, including mixtures of aberrations, like coma plus astigmatism. The importance of this effort is the following. Once the "status" of the radiation system is determined, and by status we mean identifying whether or not there are aberrations and which ones, we can then provide correction techniques to correct or minimize the known aberrations. These correction techniques, in turn, include, e.g., applying corrective or compensative forces to the imaging device, or some other component of the radiation system, by way of force actuators. Alternatively, the correction techniques can include a post-operative capability to process and compensate image degradation by way of, e.g., appropriate software programs.

We indicate above that the aberrations can be described quantitatively in terms of radiation phase variations over the entrance pupil. It is possible to compute the desired radiation phase variations (as well as the amplitude) at the image plane in accordance with the well-known Fourier Transform. Thus, in a "forward" application of a two-dimensional Fourier Transform of a wavefront having a known amplitude and phase variations over the entrance pupil, one derives the amplitude and phase variations of the radiation wavefront at the image plane. Moreover, in an "inverse" application of the two-dimensional Fourier Transform, the wavefront aberrations over the entrance pupil can be completely *reconstructed* from a known amplitude and phase of the radiation field in the image plane.

In practice, this wavefront "reconstruction" can be effected in the following two-fold way. First, an image plane sensor, for example a detector array comprising a matrix of photodiodes, each of which photodiodes provides a signal of magnitude related to the intensity of the radiation field incident thereon, can be employed to develop an intensity point spread function (PSF). Now, the PSF may be defined as the magnitude squared of the Fourier Transform of the wavefront that represents the aberrated wavefront at the entrance pupil of the imaging device. In general, however, the resulting PSF contains only magnitude or amplitude information, and this amplitude information is *not* sufficient to reconstruct the wavefront aberrations over the entrance pupil. Accordingly, secondly, interferometric techniques, including Twyman-Green or Fizeau interferometers, may be employed to capture the image plane phase information. In consequence, by way of the two-dimensional inverse Fourier Transform, the wavefront aberrations over the entrance pupil can be completely reconstructed from the (now) known amplitude and phase of the radiation in the image plane.

Recall that we are working on the problem of determining whether or not the imaging device may have introduced aberrations into the radiation field. This is another way of stating that, initially, we cannot avail ourselves of the forward application of the Fourier Transform to determine the phase variations (if any) in the image plane, since we do not yet know what is the wavefront function at the entrance pupil. Moreover, in terms of the inverse use of the Fourier Transform, we have found it impractical to employ an interferometer to capture the image plane phase information, since it may be quite difficult in a real world environment to replicate laboratory conditions that are required to insure that the interferometer has stringent vibration isolation, and satisfies coherence limitations. In short, we have the problem of determining aberrations reconstructed on the basis of data provided by the image plane sensor, alone. This problem may be restated in the following way: determine the entrance pupil plane phase aberrations from a knowledge of an image-plane intensity distribution, e.g., an intensity point spread function.

It is observed that calculating the phase aberrations from the image-plane intensity distribution is ill-posed, because of an inherent loss of (phase) information by the image plane sensor. Accordingly, the problem to be solved, "phase-retrieval", requires additional information or system constraints on the entrance pupil wavefront and its aberrations.

One type of constraint within the context of phase-retrieval is to *assume* that the geometry and wavefront amplitude distribution over the entrance pupil *are* known. Additionally, one can also assume thaat the phase aberrations are representable parametrically; e.g., in terms of a Zernike polynomial. These constraints reduce the problem to one whose solution can be expressed in terms of a finite number of unknown parameters.

Under the assumption of an adequate parametric model, the phase-retrieval problem can be solved by finding the parameter values which, when put through the forward Fourier Transform, produce the measured image data. Conceptually, the correct set of parameter values can be obtained via an exhaustive search. In practice, however, such an approach may not be feasible, and efficient strategies need to be developed for searching a parameter space.

We have now discovered a different approach to developing an efficient search strategy. In sharp contrast to known techniques for addressing the phase retrieval problem on its own terms, namely, searching a parameter space for the phase and/or estimating a phase and then iteratively improving the estimate, we provide a method and system for wavefront reconstruction from the image plane intensity distribution. Accordingly, in a first aspect, the present invention provides a novel method to be employed in conjunction with a radiation system, the radiation system comprising:

(1) at least one source of radiation;

(2) at least one imaging device for imaging at least a portion of the radiation emitted by the or each source onto at least one image plane;

the or each imaging device functioning to produce at the image plane an intensity distribution profile; and (3) a detector array located at the image plane for realizing the intensity distribution profile;

the method comprising the steps of:

(a) defining a feature vector derived from the intensity distribution profile; and (b) employing an adaptive computational architecture for associating the feature vector with at least one identifying characteristic of a selected imaging device.

One advantage of the novel method is that it can be employed to provide real time corrections of the radiation system, based upon the or each identifying characteristic of the selected imaging device. For example, the method can determine that the imaging device, say a mirror, has an identified characteristic, such as a given amount of trefoil. Accordingly, the force actuators disclosed above may be used to provide real time corrections to the mirror.

Another important advantage of the method is that the adaptive computational architecture has an inherent learning capability. That is, the association between an arbitrary feature vector derived from the intensity distribution profile, and the identified characteristics of the imaging device, may be obtained by training from previously analyzed examples. As discussed below, the training may advantageously include, e.g., an employment of neural networks and/or statistical algorithms and methods, for associating a feature vector with a known characteristic of the imaging device. The training capability, in turn, implies that the novel method can be exploited to accommodate and correct critical changes in the radiation system, including new characteristics of an imaging device.

The first method step of defining a feature vector derived from the intensity distribution profile subsumes the following general considerations. In one embodiment, the intensity distribution profile recorded by imaging a point source on a charge coupled device, or other recording media, is the point spread function. A feature vector comprising spatial moments, as described in detail below, may be derived from the point spread function. Alternatively, the intensity distribution profile recorded from an extended source may be used to derive the feature vector comprising power spectral components.

The second method step of employing an adaptive computational architecture for associating the feature vector with at least one identifying characteristic of the imaging device subsumes the following general considerations. The adaptive computational architecture preferably is non-linear, although it may be linear. As indicated briefly above, the architecture provides a learning capability, and this may be realized by statistical learning algorithms, and/or a preferred employment of neural network technology, as discussed in detail below.

In a second aspect, the present invention provides a novel radiation system comprising:

(1) at least one source of radiation;

(2) at least one imaging device for imaging at least a portion of the radiation emitted by the or each source onto at least one image plane;

the or each imaging device functioning to produce at the image plane an intensity distribution profile;

(3) a detector array located at the image plane for realizing the intensity distribution profile;

(4) means for defining a feature vector derived from the intensity distribution profile; and (5) means for associating the feature vector with at least one identifying characteristic of a selected imaging device.

We now briefly address some preferred features of the novel radiation system.

The source of radiation preferably comprises a single point source emitting monochromatic radiation. It may, however, also be an extended source. The source of radiation may subsume the entire electromagnetic spectrum, although preferably, the source of radiation is defined by the optical band of frequencies. The imaging device may comprise, for example, a lens, a mirror or a spatial grating, as appropriate. The detector array preferably comprises a matrix comprising charge coupled devices, although, for example, an array of photodiodes may be alternatively employed. The two means elements (4) and (5) may be realized by software comprising a series of Fortran subroutines and functions. An illustrative software program is set forth below in an Example.

BRIEF DESCRIPTION OF THE DRAWING

The invention is illustrated in the accompanying drawings in which.

DETAILED DESCRIPTION OF THE INVENTION

Figure 1:
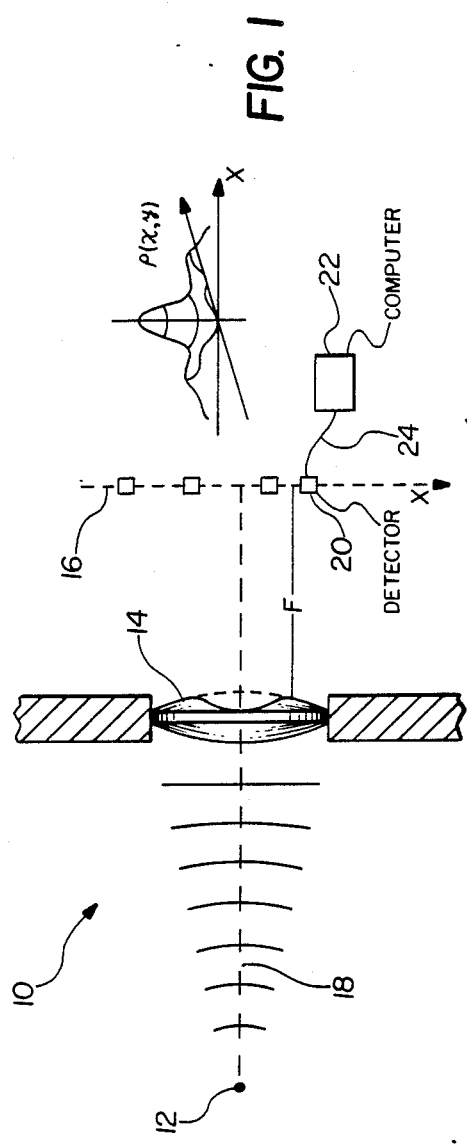
FIG. 1 shows a radiation system of the present invention.

Attention is now directed to FIG. 1, which shows an optical system 10 of the present invention. The system 10 includes a single point source 12 emitting monochromatic optical radiation. In particular, the source 12 is a continuous-wave helium-neon gas laser at 632.8 nm. The system 10 also includes a lens 14 located at the system 10 entrance pupil. The lens 14 functions to image the optical radiation at a far field focal plane 16. The focal plane 16 is located at a plane orthogonal to an optical axis 18 defined by the source 12 and lens 14. A detector array 20 comprising a 64×64 matrix of conventional charge-coupled devices is located at the focal plane 16. The F# of the system 10, as conventionally defined, is approximately 18.

During system 10 operation, the radiation that is imaged by the lens 14 is detected by the detector 20. The output of the detector 20 provides an intensity distribution profile, here given as a point spread function defined by the equation (1)

$$\rho = \rho(x,y) \tag{1}$$

The point spread function (1) is inputted to a Microvax II computer 22 along a line 24. The computer 22 may be programmed to modify the point spread function in a manner disclosed immediately below, and in order to define a feature vector and simulate an adaptive computational architecture.

Preferably, the point spread function may be modified in several ways, in preparation for the first step of the method of the invention, namely, defining a feature vector derived from the point spread function. Accordingly, the function $\rho$ may be modified by a weighting function, and may be windowed, in order to account for the fact that the detector array 20 is of limited extent.

As summarized above, the method of the present includes a first step of defining the feature vector. The feature vector, in turn, may be derived from the (modified) point spread function. In particular, the feature vector is preferably defined as one derived by way of another intermediary, namely, a multi-dimensional moment vector. The moment vector, in turn, subsumes the point spread function as shown mathematically in an equation (2) below.

The usefulness of the moment vector as a feature vector is at least two-fold. First, when an aberration type exhibited by the lens 14 is substantially isolated, for example, only hexafoil, the point spread function exhibits certain characteristic symmetries, independent of the amount of the aberration. These symmetries include, for example, invariance to translation, position and scale, etc. This symmetry-invariance fact, in turn, may be exploited by moment vectors, to the end of discriminating among different point spread functions, and thereby identifying a particular aberration. In more complex cases, for example when the lens 14 introduces mixtures of several aberration types, the basic symmetry patterns in the point spread function may be vitiated. Nevertheless, even for the complex cases, moment vectors are useful since they reduce the dimensionality of the recognition problem, i.e., the efficient discrimination among different point spread functions to the end of identifying the salient aberrations. Moreover, the use of moment vectors is preferred, since they positively address important issues including numerical stability of the discrimination estimates, changes in overall system image intensity, amendability to parallel processing, and favorable sensitivity to noise and higher order aberrations.

The moment vectors preferably are defined by the following equation (2):

$$M_{pq} = \int\int x^p y^q \rho_n(x,y) dx dy \tag{2}$$

In accordance with equation (2) and preferred aspects of the method of the invention, a set of n lenses 14, each having known aberrations, may be individually inserted into the optical system 10. This action produces n known point spread functions. The n known point spread functions $\rho_n(x,y)$ may be each individually developed by way of the moment vector equation (2), to produce n feature vectors. Thus, for any one known point spread function, for example, $\rho_1(x,y)$, a column feature vector $FV_1$ can be calculated from equation (2), and of the form:

$$\text{Feature vector } FV_1 = \begin{bmatrix} M_{00} \\ M_{10} \\ M_{01} \\ M_{11} \\ \cdot \\ \cdot \\ \cdot \\ M_{pq} \end{bmatrix} \tag{3}$$

In a similar manner, a second known point spread function $\rho_2(x,y)$ can be developed by way of equation (2), to form a second column feature vector $FV_2$. This procedure may be repeated to form an exhaustive array of column feature vectors corresponding to n point spread functions. Further instruction on these points is provided by Ming Kuei Hu, "Visual Pattern Recognition By Moment Invariants", IRE Transactions On Information Theory, pp. 179–187, February 1962; and Michael Reed Teague, "Image Analysis Via The General Theory Of Moments", J. Opt. Soc. Am., Vol 70., No. 8, August, 1980, pp. 920–930.

The elements of each column feature vector (equation 3) correspond to a (p+q) phase space. In this embodiment, the feature vector being used is the list of moments derived from the point spread function. The adaptive computational architecture of the present invention calculates from the list of moments the corresponding sets of aberrations, e.g., hexafoil, or power+-coma.

We now summarize the above materials on preferred aspects of the first step of the present method, in preparation for disclosing the details of the second step of the method:

(1) a set of n different lenses 14 having known aberrations may be serially inserted into the optical system 10, to yield n unique point spread functions (Equation 1);

(2) each of the n point spread functions corresponds to a known set of aberrations; and (3) each known point spread function may be expressed as a unique column feature vector, equation (3).

Figure 2:
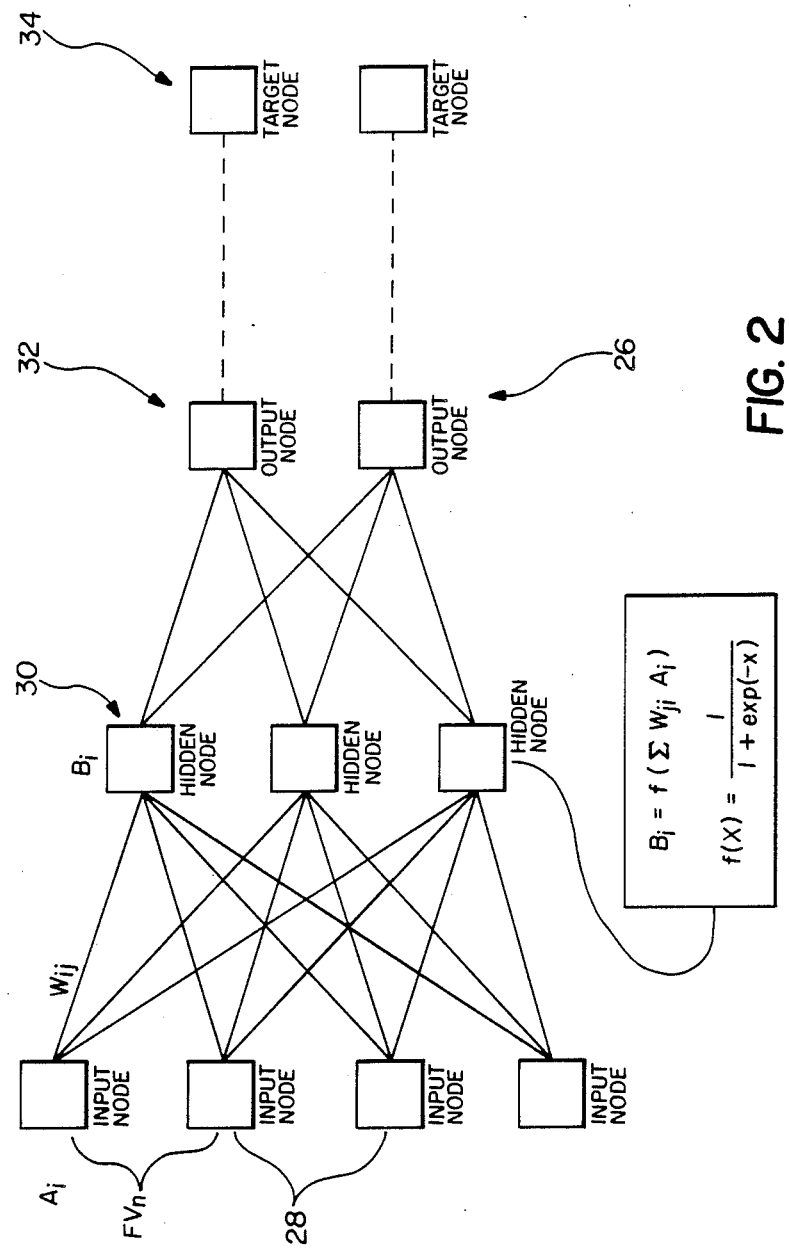
FIG. 2 shows a neural network for employment with the method and radiation system of the present invention.

The first step of the present method, so summarized in its preferred aspects, we segue to the second step which requires employing an adaptive computational architecture for associating the feature vector with at least one identifying characteristic of the imaging device, here, lens 14. A preferred such architecture comprises a three-layered non-linear neural network, of the type shown in FIG. 2. The FIG. 2 shows a neural network 26 which comprises a plurality of column input nodes 28, for inputting the column feature vector; a plurality of non-linear column hidden nodes 30, each of which nodes accepts adjustable, weighted input signals $w_{ij}$ from each of the input nodes 28; a plurality of column output nodes 32, each of which output nodes accepts adjustable, weighted input signals $w_{kl}$ from each of the hidden nodes 30; and, finally, a plurality of column target nodes 34 which are individually mated to each of the output nodes 32.

The functioning of the neural network 26 can be explained in overview by understanding its operation during a preliminary "learning" mode, and a subsequent real-time processing mode.

In the preliminary mode, the neural network 26 functions as an "off-line" training or learning vehicle, to build up a *recognizable* "vocabulary" between, on the one hand, known aberration feature vectors as inputs to the column input nodes 28, and on the other hand, known target node 34 aberration parameters. The "training" or "learning" per se is accomplished by iteratively adjusting the weighting factors $w_{ij}$ and $w_{kl}$, to the end that properly adjusted weighting factors insure that approximate aberration types and magnitudes in the output nodes 32 correspond (within an error criteria) to the known target node 34 aberration parameters. In particular, the neural network 26 works "backward", from $w_{kl}$ to $w_{ij}$, hence the expression back propagation, to "learn" the required new weights. Moreover, the "learning" is accumulative, in the sense that weights are learned for each of a succession of input feature vectors, and each succession of input feature vectors adds cumulatively to the codified repository of the weighting factors. (In this manner, by the way, the neural network 26 can theoretically "learn" the entire vocabulary of Zernike aberrations).

In the second mode, the neural network 26 provides a real-time processing capability. The neural network 26 accepts an arbitrary input feature vector as an input to the column nodes 28; and computes an output node 32 column vector that characterizes a heretofore unknown intensity distribution profile, e.g., a particular aberration magnitude. Here, in the real-time processing mode, the cumulatively codified weighting factors, built up during the learning mode, provide a basis against which the arbitrary input feature vector may be interrogated.

With this overview of the two-fold functioning of the neural network 26 in mind, we now turn to particular details of its operation. Accordingly, in the initial learning mode, a first feature vector corresponding to a known aberration, of the form (FV$_1$) expressed by the column vector equation (3) above, is provided as an input to the column input nodes 28, so that each element of the column vector equation (3) is placed on a one-to-one basis with the column input nodes 28. Next, each element placed in the column input nodes 28, is operated upon by the adjustable, weighted function $w_{ij}$, as preparation for input to the appropriate hidden node column 30. Initially, the weights are preferably an arbitrary scalar, selected randomly in a small interval around zero, e.g., in an interval form −0.01 to 0.01.

The node value $B_j$ on the $j^{th}$ second layer 30 node are computed by:

$$B_j = f(\Sigma w_{ij} z_j) \quad (4)$$

where $z_j$ is the contents of the first layer 28 node number j (equal to the $j^{th}$ component of the input feature vector, except that $z_0$ equals 1), and where f is an "activation function" preferably of the form:

$$f(x) = 1/(1 + \exp(-x)) \quad (5)$$

The computed values $B_i$ represent the output of the hidden node column 30. These values are operated on by the adjustable weights $w_{kl}$ connecting layer 30 with layer 32, in the same manner as above. The second weighting operation produces the output parameters stored in the column output nodes 32.

Since we are in the learning mode, the output parameters are compared to the known aberration parameters stored in the target nodes 34. If the output parameters are equal to the aberration parameters, within an error criteria, than it is understood that the arbitrary selected weights are in fact correct. On the other hand, if the output parameters are not equal to the target aberration parameters, within the error criteria, then it is understood that the arbitrary selected weights are not optimal, and must be adjusted by the backward propagation process, for further evaluation of output parameter-/aberration parameter correspondence. This process is continued, that is, new weights are learned, until the indicated correspondence is within the error criteria.

The learning mode is initialized with the processing of a first feature vector FV$_1$. With this step completed, the process may be repeated anew for a second feature vector FV$_2$, and then again repeated anew for FV$_3$, FV$_4$, FV$_n$. Note that each new learning step not only learns, in and of itself, but also carries over the learning built up by all the previous steps. Note further that the learning process can be enhanced by extending the length of the feature vector, by way of equation (3) above, and routinely extending the neural network 26 columns 28–34. By enhancement, we mean that an ever larger number of the Zernike aberrations can be learned by the neural network 26.

With the learning mode completed, the method of the present invention operates in a real time processing mode. As indicated above, this includes deriving a feature vector preferably by way of a moment analysis of an arbitrary point spread function. The PSF numerical parameters can be ascertained by way of the detector array 20, but it is presently unknown what, if any aberrations may have been introduced into the optical system 10 by way of the lens 14, and thereby become embedded in the PSF.

According to preferred aspects of the method, the aberrations may be ascertained by expanding the arbitrary PSF by way of the moment equation (2) above. This results in a feature vector of the form of equation (3) above. The prepared feature vector next becomes an input to the neural network 26. The neural network 26 processes the instant feature vector in a manner entirely analogous to the processing of a known feature vector in the training mode. One difference, however, between the two processing procedures, is that in the processing of the instant feature vector, the output parameter located in the column vector 32 nodes characterizes the sought for information on what aberration may be embedded in the point spread function. Accordingly, no present use is made of the plurality of column target nodes 34.

It is disclosed above that the adaptive computational architecture, of which the FIG. 2 neural network 26 is an important type, may also be realized by a statistical learning algorithm. We now turn our attention to this second type of architecture with the following overview.

The statistical learning algorithm (SLA) shares with the neural net approach the preferred employment of feature vectors derived from the moment equation (2). It differs from the neural network approach in that it purports to classify an arbitrary feature vector by whether or not it falls into known *discrete* regions in a multi-dimensional space. On the one hand, if the arbitrary feature vector is determined to be located in a particular region, then the sought for information on how the arbitrary feature vector is to be characterized, becomes, in fact, known. On the other hand, if the arbitrary feature vector is determined to fall outside a region, statistical criteria provided below may be used to determine an estimate as to which region the arbitrary feature vector is best associated. The statistical learning algorithm "learns" by giving ever better definition to the boundaries or envelope of each of the discrete regions. With this overview of the statistical learning algorithm in mind, we now elaborate firstly on a preliminary learning mode, and secondly on a subsequent real-time processing mode.

Figure 3:
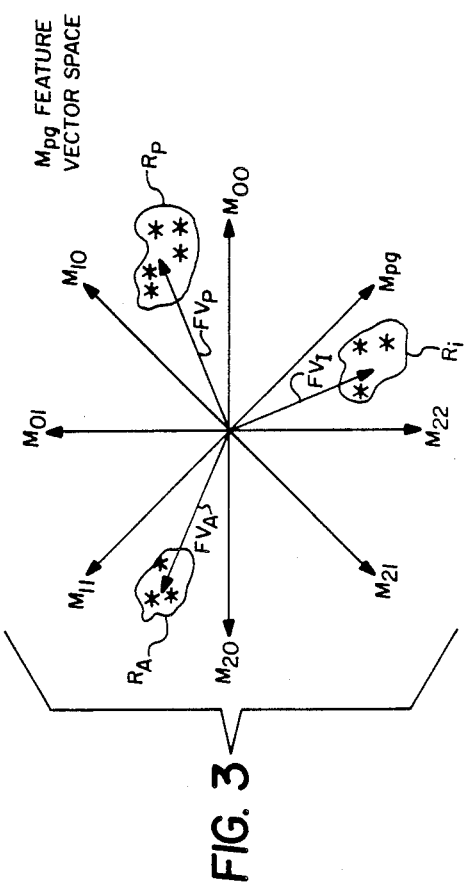
FIG. 3 shows a multi-dimensional feature vector space used in a statistical learning algorithm of the present invention.

To this end, attention is directed to FIG. 3, which shows a multi-dimensional $M_{pq}$ feature vector space. In particular, each axis in the multi-dimensional space is dedicated to a moment parameter defined by way of Equations (2) and (3) above. FIG. 3 also shows a number of discrete and independent regions $R_i$ embedded in the multi-dimensional $M_{pq}$ feature vector space. Each region is dedicated to a selected Zernike aberration, for example, power, or coma, or astigmatism, or combinations of Zernike aberrations, like trefoil and astigmatism.

The learning mode, as indicated above, includes giving ever better definition to the boundaries or envelope of each of the discrete regions $R_i$. This, in turn, may be effected in the following way. First, a known imaging device, say a lens 14 of the optical system 10 of FIG. 1, is inserted into the optical system 10 to produce a known point spread function, e.g., a PSF corresponding to power. Then, the known point spread function is developed by way of Equations (2) and (3) above, to produce a known feature vector $FV_p$ located in the multi-dimensional space $M_{pq}$. The tip of this feature vector $FV_p$ locates a power region. The boundaries or envelope of the power region are given ever greater definition by repeating the immediately foregoing analysis, but this time, by adding noise components to the moment analysis (shown as asterisks in FIG. 3). Statistical algorithms may be advantageously employed to deduce appropriate noise components. The addition of the included noise components around the known feature vector $FV_p$, effects the further articulation or definition of the power region. It is to be noted that the region is defined as to aberration, as well as to magnitude, e.g., aberration=power; magnitude=0.50 wave.

The learning mode may be continued by essentially repeating the above procedure, but this time, inserting a second lens into the optical system 10, to produce a second known point spread function, e.g., a PSF corresponding to astigmatism. Briefly, the repeat procedure involves developing a second feature vector $FV_A$ by way of Equations (2) and (3) above, to locate an astigmatism region. The boundaries or envelope of the astigmatism region are given ever greater definition by the statistical noise procedures outlined above. This results, finally, in an astigmatism region defined as to content, as well as magnitude.

The learning mode may be further continued in this manner, mutatis mutandis, to (theoretically) learn any desired set pof Zernike aberrations which are set off by independent and discrete regions, including combinations of aberrations and their magnitudes.

The statistical learning algorithm, in its subsequent real-time processing mode, works in the following way. An unknown imaging device, e.g., a lens of FIG. 1, is inserted into the optical system 10 to produce an arbitrary point spread function. As in the case of the neural network 26 above, the point spread function numerical parameters can be ascertained by way of the detector array 20, but it is presently unknown what, if any aberrations may have been introduced into the optical system 10 by way of the instant lens, and thereby become embedded in the PSF.

According to preferred aspects of the method, the aberrations may be ascertained by expanding the arbitrary PSF by way of the moment equations (2) and (3) above. This results in a feature vector located in the multi-dimensional feature vector space $M_{pq}$. If the feature vector is located in a particular region defined by the above learning mode, then the sought for information on how the instant feature vector is to be characterized, becomes an ascertained fact. On the other hand, if the instant feature vector falls outside of the learned regions, the following preferred statistical criteria may be used to determine which region the instant feature vector is best associated.

For example, consider the instant feature vector $FV_I$ in FIG. 3. We are required to define a probability model for describing the learned regions, and for associating the instant feature vector $FV_I$ with respect to the learned regions.

A preferred probability model (1) uses Bayesian inference to assess the probability that the instant feature vector belongs to a particular region; (2) assumes that the individual regions are describable by multivariate Gaussian functions; and (3) assumes that the "prior probabilities" of the region classes are equal. These three points are now developed.

Bayesian Determination of Classification Probabilities

Assume that the regions are describable by well-defined probability density functions $p_j(f)$, which give the conditional probability that the feature vector of an object is f, given that the object belongs to class $k_j$.

Then, given that an object has feature vector f, an approach to the classification problem is to determine the probability that the object belongs to each class $k_j$, by using Bayes's law. The resulting probabilities can then be compared, to determine the most likely classification of the object.

The application of Bayes's law requires that prior probabilities $pr_j$ exist, giving the distribution of objects among the classes, unconditioned by knowledge of the feature vectors of the objects.

In more detail, the conditional probability $p(j|f)$ that the object is in class $k_j$, given that it has feature vector f, is given by:

$$p(j|f) = p_j(f)pr_j/(p_1(f)pr_1 + p_2(f)pr_2 + \ldots p_K(f)pr_K)$$

using Bayes's law, where $pr_j$ is the prior probability that the object falls within class $k_j$.

The application of this procedure to classifying an unknown object 0 is to determine its feature vector f, determine the associated conditional probability density values $p_j(f)$ (by substitution in the analytical form for $p_j$), use the formula above to compute the $p(j|f)$'s, and compare these answers with each other to determine the most likely classification of 0.

Multivariate Gaussian Regions

To carry through this procedure, the conditional probability densities $p_j$ must be known, or at least approximated. The conditional probabilities $p_j$ specify the probability distribution associated with the class $k_j$;

these determine the shape of the cluster or region associated with $k_j$ in the feature vector space.

A very common procedure is to approximate each $p_j$ as a multidimensional Gaussian distribution; that is, to assume the form:

$$p_j(f) = (2\pi)^{-d/2} |\Sigma|^{-\frac{1}{2}} \exp[-(\tfrac{1}{2})(f-\mu_j)^t \Sigma_j^{-1}(f-\mu_j)],$$

where $\mu_j$ and $\Sigma_j$ are the (vector) mean and covariance matrix of the distribution and d is the dimension of the feature vector space. Here $|\Sigma_j|$ is the determinant of $\Sigma_j$, and a superscripted t donates the transpose of a (column) vector. (By definition $\mu_j$ is the expectation value of f, and $\Sigma_j$ is the expectation value of $(f-\mu_j)(f-\mu_j)^t$, for f drawn from the distribution.) Thus, the approximation of $p_j$ as a multivariate Gaussian permits it to be specified by the set of p components of $\mu_j$ plus the set of $p(p+1)/2$ independent components of $\Sigma_j$.

This assumption models each region as having an ellipsoid shape in feature vector space. The eigenvectors of the covariance matrix correspond to the principal axes of the ellipsoid. The shape and orientation of the ellipsoids are in this way determined from the covariance matrix, while the mean vector of the region determines the position of the ellipsoid.

Specification of Prior Probabilities

Use of the Bayes's rule requires, in addition to the conditional probability densities, a specification of the prior probabilities $pr_j$. The simplest assumption is that all the prior probabilities are equal with $pr_j = 1/k$. Performance can, of course, be improved if more accurate estimates of the prior probabilities are known. In the current application, the equality of prior probabilities is assumed.

Discriminant Functions for the Regions

The conditional probability $p(j|f)$ is precisely the probability that the class associated with a specified feature vector f is $k_j$. Once the means, covariance matrices, and prior probabilities are specified, the reasoning given in the preceding section shows that this probability is easily computable. This conditional probability $p(j|f)$ can be thought of as a discriminant function $\alpha_j(f)$ associated with the class $k_j$, in that the $\alpha_j(f)$ that is maximal determines the classification of f.

In practice it is usually convenient to apply some monotonic function to $p(j|f)$ to define the discriminant function. In particular, by taking the natural logarithm of $p(j|f)$ the exponential in the expression for $p_j(f)$ can be avoided. Also, since the denominator of the expression for $p(j|f)$ is independent of j the denominator can be ignored in defining the discriminant function. Thus, a suitable discriminant function is defined as:

$$\alpha_j(f) = \ln(p_j(f)) + \ln(pr_j),$$

and, if all the prior probabilities are assumed to be equal, even the $\ln(pr_j)$ term can be eliminated, giving $\alpha_j(f) = \ln(p_j(f))$, or:

$$\alpha_j(f) = \ln((2\pi)^{-d/2}|\Sigma_j|^{-\frac{1}{2}}) - (\tfrac{1}{2})(f-m_j)^t \Sigma_j^{-1}(f-\mu_j),$$

This form has the advantage of eliminating some unnecessary calculations, and of avoiding the danger of floating point underflows in the classification calculation.

EXAMPLE

This Example includes a listing of a multi-dimensional moment-based classification software program developed in accordance with the method of the present invention. The software consisted of a series of FORTRAN subroutines and functions. The software made use of a set of 17 data files, which are described here as well.

The routines were assumed to be called from a general main program. All communication with the supplied subroutines was through the argument list of the single subroutine CLASSIFICATION, presented here first, which calls other sub-programs as needed.

CLASSIFICATION takes six arguments, as follows:

IMAGE_ARRAY_INT—a SIZE by SIZE 4-byte integer array containing the point spread function to be analyzed.

DX=distance in inches between detector elements (the spacing is here assumed to be the same in both directions). The nominal value for DX is $2.6672 \times 10^{-4}$ (inches per sample).

WAVELENGTH—wavelength, in inches. The nominal value in nanometers is 632.8 nm, which converts to $2.4920 \times 10^{-5}$ inches.

FNUM—F number of the system. The nominal value is 18.0.

SIZE—linear dimension of IMAGE$_{13}$ ARRAY INT. The nominal value is 64.

LUN—an available FORTRAN logical unit number.

The logical unit number was provided in order that the program could read the supplied data files. These data files contained the statistics that describe the multi-dimensional regions (clusters). (The advantage of providing this data in data files rather than hardcoded in the software was that the number and type of aberration classes could be easily modified by changing the data files (without the necessity of modifying the code). CLASSIFICATION currently contains a hardcoded reference to the first of these data files, CASES.DAT, which contains a list of the names of the other data files used.

The data files were as follows:

CASES.DAT—Number of classes, and names of the data files (containing the class statistics) to be read by the software.

CASE_0.DAT—Statistics for diffraction limited point spread function.

CASE_1.DAT—Statistics for 1 wave Trefoil.

CASE_2.DAT—Statistics for 0.25 wave Astigmatism.

CASE_3.DAT—Statistics for 0.50 wave astigmatism.

CASE_4.DAT—Statistics for 0.75 wave Astigmatism.

CASE_5.DAT—Statistics for 0.25 wave Coma.

CASE_6.DAT—Statistics for 0.50 wave Coma.

CASE_7.DAT—Statistics for 0.75 wave Coma.

CASE_8.DAT—Statistics for 0.50 wave Trefoil with 0.50 wave Astigmatism.

CASE_9.DAT—Statistics for 0.50 wave Trefoil with 0.75 wave Astigmatism

CASE_10.DAT—Statistics for 0.50 wave Coma with 0.50 wave Astigmatism.

CASE_11.DAT—Statistics for 0.50 wave Coma with 0.75 wave Astigmatism.

CASE_12.DAT—Statistics for 0.50 wave Trefoil with 0.50 wave Coma.

CASE_13.DAT—Statistics for 0.50 wave Trefoil with 0.75 wave Coma.

CASE_14.DAT—Statistics for 0.75 wave Trefoil with 0.75 wave Coma.

CASE_15.DAT—Statistics for 0.75 wave Astigmatism with 0.75 wave Trefoil.

Each of the data files CASE_0.DAT through CASE_15.DAT was prepared from a set of simulated sample point spread functions, with added random defocus and noise. Each data file contained a one line description of the aberration type, the length of the feature vector being used (12), a list of the mean values of each feature, the determinant of the covariance matrix, and the elements of the (12 by 12) inverse covariance matrix. Because the first invariant moment would be identically 1 by definition (because of the normalization), the first invariant moment was replaced with the entropic size, normalized by dividing by the wavelength times the F number.

The subroutine and functions listed here were all included in a single file, CLASSIFIER.FOR, on a tape. The data files were not listed here, but were included on the same tape, with names and content as described above.

```
        SUBROUTINE CLASSIFICATION(IMAGE_ARRAY_INT,DX,WAVELENGTH,
     1       FNUM,SIZE,LUN)
C       IMPLICIT NONE
        INTEGER MAX_SIZE
        INTEGER MAX_NUM_CLASSES
        PARAMETER (MAX_SIZE=128,MAX_NUM_CLASSES=30)

INTEGER SIZE
        INTEGER NUM_CLASSES
        REAL DX,WAVELENGTH,FNUM
        REAL IMAGE_ARRAY(MAX_SIZE*MAX_SIZE)
        INTEGER IMAGE_ARRAY_INT(SIZE,SIZE)
        INTEGER I
        CHARACTER*80 SET_NAME(MAX_NUM_CLASSES)
        CHARACTER*80 DESCRIPTION(MAX_NUM_CLASSES)
        INTEGER LUN
        INTEGER CLASSIFY

OPEN (UNIT=LUN,FILE='CASES.DAT',STATUS='OLD')
        READ (LUN,*) NUM_CLASSES

DO 55 I=1,NUM_CLASSES
            READ (LUN,'(A)') SET_NAME(I)
55      CONTINUE

C       WORK WITH REAL ARRAY:
        CALL CONVERT_TO_REAL(IMAGE_ARRAY,IMAGE_ARRAY_INT,
     1       SIZE,SIZE)

C       DO THE CLASSIFICATION:
        CALL CLASSIFY(IMAGE_ARRAY,DX,WAVELENGTH,FNUM,
     1       SIZE,SET_NAME,NUM_CLASSES,DESCRIPTION,LUN)

RETURN
        END

SUBROUTINE CONVERT_TO_REAL(RIMAGE,IMAGE,NROWS,NCOLS)
C       IMPLICIT NONE
        INTEGER NROWS,NCOLS
        INTEGER IMAGE(NROWS,NCOLS)
        REAL RIMAGE(NROWS,NCOLS)

INTEGER ROW,COL

DO 100 ROW=1,NROWS
```

```fortran
            DO 50 COL=1,NCOLS
                RIMAGE(NROWS,NCOLS) = IMAGE(NROWS,NCOLS)
50      CONTINUE
100     CONTINUE

RETURN
        END

SUBROUTINE CLASSIFY(IMAGE_ARRAY,DX,WAVELENGTH,FNUM,
     1      SIZE,SET_NAME,NUM_CLASSES,DESCRIPTION,LUN)
C       IMPLICIT NONE

INTEGER NUM_MOMENTS,MAX_NUM_CLASSES
        REAL WEIGHT
        PARAMETER (NUM_MOMENTS=12,WEIGHT=1.72,MAX_NUM_CLASSES=30)

INTEGER SIZE
        INTEGER NUM_CLASSES
        REAL DX,WAVELENGTH,FNUM
        REAL IMAGE_ARRAY(SIZE,SIZE)
        REAL PHI(NUM_MOMENTS)
        REAL ANGLE,ENTROPIC_LENGTH
        INTEGER I
        CHARACTER*80 SET_NAME(NUM_CLASSES)
        CHARACTER*80 DESCRIPTION(NUM_CLASSES)
        INTEGER LUN
        COMPLEX INVAR(0:4,0:4)
        REAL INV_COV(NUM_MOMENTS,NUM_MOMENTS,MAX_NUM_CLASSES)
        REAL DET_COV(MAX_NUM_CLASSES),MEAN(NUM_MOMENTS,MAX_NUM_CLASSES)
        REAL PRIOR_PROBABILITY(MAX_NUM_CLASSES)
        INTEGER CLASSIFICATION
        REAL LOG_LIKELYHOOD
        REAL CONFIDENCE
        INTEGER CLASS_DECISION

DO 55 I=1,NUM_CLASSES
            CALL READ_COV_STATISTICS(LUN,SET_NAME(I),MEAN(1,I),
     1          INV_COV(1,1,I),
     1          DET_COV(I),NUM_MOMENTS,DESCRIPTION(I))
            PRIOR_PROBABILITY(I) = 1.0/NUM_CLASSES
55      CONTINUE

CALL MOMENT(IMAGE_ARRAY,SIZE,PHI,
     1      INVAR,
     1      ENTROPIC_LENGTH,DX,WEIGHT,ANGLE,WAVELENGTH,FNUM)

CLASSIFICATION = CLASS_DECISION(PHI,MEAN,INV_COV,
     1      DET_COV,NUM_MOMENTS,
     1      PRIOR_PROBABILITY,NUM_CLASSES,CONFIDENCE)

WRITE (*,777)
        WRITE (*,777) 'CLUSTER ANALYSIS'
        WRITE (*,777) 'Point Spread Function is of Type:'
        WRITE (*,777) DESCRIPTION(CLASSIFICATION)
        WRITE (*,778) 'with a Confidence Level of',CONFIDENCE,'%.'
        WRITE (*,777)
```

```
777     FORMAT (1X,A)
778     FORMAT (1X,A,1X,F5.1,A2)
        RETURN
        END

INTEGER FUNCTION CLASS_DECISION(FEATURE,MEAN,INV_COV,DET_COV,
     1        DIMENSION,
     1        PRIOR_PROBABILITY,NUM_CLASSES,CONFIDENCE)
C       IMPLICIT NONE

INTEGER NUM_CLASSES,I
        INTEGER DIMENSION
        REAL FEATURE(DIMENSION)
        REAL INV_COV(DIMENSION,DIMENSION,NUM_CLASSES)
        REAL DET_COV(NUM_CLASSES)
        REAL MEAN(DIMENSION,NUM_CLASSES),CONFIDENCE
        REAL PRIOR_PROBABILITY(NUM_CLASSES)
        REAL DISCRIMINANT,TOTAL_EXP_DISC
        REAL MAX_DISCRIMINANT,NEW_DISCRIMINANT

MAX_DISCRIMINANT = -9E19
        CLASS_DECISION = 0
        TOTAL_EXP_DISC = 0
        DO 55 I=1,NUM_CLASSES
             NEW_DISCRIMINANT = DISCRIMINANT(FEATURE,
     1           MEAN(1,I),INV_COV(1,1,I),DET_COV(I),
     1           DIMENSION,PRIOR_PROBABILITY(I))
             WRITE (*,720) 'LOG LIKELYHOOD OF CLASS ',I,' = ',
     1           NEW_DISCRIMINANT - LOG(PRIOR_PROBABILITY(I))
             IF (NEW_DISCRIMINANT.GT.-20.0) THEN
                  TOTAL_EXP_DISC = EXP(NEW_DISCRIMINANT) +
     1                  TOTAL_EXP_DISC
             END IF
             IF (NEW_DISCRIMINANT.GT.MAX_DISCRIMINANT) THEN
                  MAX_DISCRIMINANT=NEW_DISCRIMINANT
                  CLASS_DECISION = I
             END IF
55      CONTINUE
        IF (TOTAL_EXP_DISC.GT.0) THEN
             CONFIDENCE = 100.0*(EXP(MAX_DISCRIMINANT)
     1                  /TOTAL_EXP_DISC)
        ELSE
             CONFIDENCE = 0
        END IF
720     FORMAT (1X,A,I2,A,G12.4)
        RETURN
        END

REAL FUNCTION DISCRIMINANT(FEATURE,MEAN,INV_COV,DET_COV,
     1        DIMENSION,PRIOR_PROBABILITY)
C       IMPLICIT NONE

INTEGER DIMENSION
        REAL FEATURE(DIMENSION)
        REAL INV_COV(DIMENSION,DIMENSION)
        REAL DET_COV
```

```
      REAL MEAN(DIMENSION)
      REAL PRIOR_PROBABILITY
      REAL LOG_NORMAL

DISCRIMINANT = LOG_NORMAL(FEATURE,MEAN,INV_COV,DET_COV,
    1        DIMENSION) + LOG(PRIOR_PROBABILITY)
      RETURN
      END

REAL FUNCTION LOG_NORMAL(FEATURE,MEAN,INV_COV,DET_COV,DIMENSION)
C     IMPLICIT NONE

REAL PI
      PARAMETER (PI=3.1415926)

INTEGER DIMENSION
      REAL FEATURE(DIMENSION)
      REAL INV_COV(DIMENSION,DIMENSION)
      REAL DET_COV
      REAL MEAN(DIMENSION)
      INTEGER ROW,COL
      REAL SUM

SUM = 0
      DO 60 ROW=1,DIMENSION
      DO 55 COL=1,DIMENSION
             SUM = SUM +
    1              (FEATURE(ROW)-MEAN(ROW))*INV_COV(ROW,COL)*
    1                     (FEATURE(COL)-MEAN(COL))
55    CONTINUE
60    CONTINUE
      LOG_NORMAL = -.5*LOG(2*PI**DIMENSION*DET_COV)-.5*SUM
      RETURN
      END

SUBROUTINE READ_COV_STATISTICS(LUN,FILE,MEAN,INV_COV,
    1        DETERMINANT,NUM_MOMENTS,DESCRIPTION)
C     IMPLICIT NONE
      INTEGER LUN,NUM_MOMENTS,I,J,NUM_MOMENTS_DAT
      REAL INV_COV(NUM_MOMENTS,NUM_MOMENTS)
      REAL MEAN(NUM_MOMENTS),DETERMINANT
      CHARACTER*80 FILE,DESCRIPTION

OPEN (FILE=FILE,UNIT=LUN,STATUS='OLD')

READ (LUN,'(1X,A80)') DESCRIPTION
      READ (LUN,778) NUM_MOMENTS_DAT
      DO 55 I=1,NUM_MOMENTS
             READ (LUN,777) MEAN(I)
55    CONTINUE

READ (LUN,777) DETERMINANT

DO 65 I=1,NUM_MOMENTS
      DO 60 J=1,NUM_MOMENTS
```

```
              READ (LUN,777) INV_COV(I,J)
60      CONTINUE
65      CONTINUE

CLOSE (LUN)

777     FORMAT (1X,G18.8)
778     FORMAT (1X,I3)

RETURN
        END

SUBROUTINE MOMENT(IN_IMAGE,SIZE,PHI,INVAR,ENTROPIC_WIDTH,SCALE1,
     1      WEIGHT,ANGLE,WAVELENGTH,FNUM)
C       IMPLICIT NONE

C       COMPUTES THE 1ST THROUGH 3D CENTRAL MOMENTS OF A DIGITAL IMAGE.
C       ALSO FINDS SEVEN INVARIANT MOMENTS (REF. GONZALES AND
C       WINTZ, P.358.), SHOWN BY HU TO BE INVARIANT UNDER ROTATION,
C       TRANSLATION, AND SCALE CHANGE.  (THE GONZALES AND WINTZ REFERENCE
C       IS, IN FACT, INCORRECT IN ITS CONSTRUCTION OF THE NORMALIZED
C       CENTRAL MOMENTS.  THIS ERROR IS CORRECTED IN THIS PROGRAM.)
C
C       MODIFIED TO INCLUDE A WEIGHTING TERM IN ORDER TO GUARANTEE THAT
C       THE MOMENTS BE WELL DEFINED.
C
C       MODIFIED TO RECALCULATE A CHARACTERISTIC LENGTH BASED UPON
C       ENTROPY
C
C       MODIFIED TO TAKE ROOTS OF THE PHI'S IN ORDER TO MAKE THE PHI'S
C       FIRST ORDER IN THE CENTRAL MOMENTS.

C       PARAMETERS
        INTEGER MAXSIZE,MAXORDER
        INTEGER LUN_IN,LUN_OUT
        COMPLEX I
        PARAMETER (LUN_IN=1,LUN_OUT=2,MAXSIZE=512,MAXORDER=4)
        PARAMETER (I=(0,1))

C       VARIABLES
        INTEGER SIZE
C           SIZE OF IMAGE
        REAL IN_IMAGE(MAXSIZE*MAXSIZE)
C           IMAGE ARRAY
        CHARACTER*80 FILE,DATAFILE
C           NAME OF IMAGE FILE
        DOUBLE PRECISION MEANX,MEANY
C           MEAN X AND Y
        DOUBLE PRECISION MU(0:MAXORDER,0:MAXORDER)
C           CENTRAL MOMENTS
        DOUBLE PRECISION ETA(0:MAXORDER,0:MAXORDER)
C           NORMALIZED CENTRAL MOMENTS
        REAL PHI(12)
C           INVARIANT MOMENTS
        COMPLEX INVAR(0:4,0:4)
        DOUBLE PRECISION MUROW(0:MAXORDER,0:MAXORDER,MAXSIZE),
```

```
    1       SUMROW(MAXSIZE),
    1       MEANXROW(MAXSIZE),MEANYROW(MAXSIZE)
            INTEGER P,Q
C           ORDER OF CENTRAL MOMENT
            DOUBLE PRECISION GAMMA
            REAL SCALE,SCALE1,TRACE,AREA,OLD_TRACE,OLD_AREA,WEIGHT
            REAL ANGLE, LENGTH, ENTROPIC_WIDTH,WAVELENGTH,FNUM
            INTEGER DATATYPE
            REAL PHASE
            INTEGER H,K
            REAL SGN

C           SCALE1 = 0.00026772
C                   INCHES
            SCALE = 1
C                   1 PIXEL

C           WEIGHTING SCALE FACTOR
C           WEIGHT = 1.72

C           COMPUTE CENTROIDS OF ORIGINAL IMAGE
            CALL FIND_MEANS(MEANX,MEANY,IN_IMAGE,SIZE,SIZE,
    1           SUMROW,MEANXROW,MEANYROW)

C           COMPUTE CENTRAL MOMENTS OF ORIGINAL IMAGE (TO SECOND ORDER)
C           CALL FIND_CENTRAL_MOMENTS(MU,MAXORDER,IN_IMAGE,SIZE,SIZE,MEANX,
C   1           MEANY,SCALE,MUROW)

C           NORMALIZE IMAGE TO HAVE VOLUME = 1
            CALL VOLUME_ONE(IN_IMAGE,SIZE,SIZE)

C           COMPUTE CHARACTERISTIC SIZE BY EXAMINING ENTROPY
            CALL ENTROPIC_LENGTH(LENGTH,IN_IMAGE,SIZE,SIZE)
            ENTROPIC_WIDTH = LENGTH*SCALE1

C           WEIGHT IMAGE WITH WEIGHTING FUNCTION
            CALL WEIGHT_IMAGE(IN_IMAGE,SIZE,SIZE,MEANX,MEANY,
    1           LENGTH/WEIGHT)

C           COMPUTE CENTROIDS OF WEIGHTED IMAGE
            CALL FIND_MEANS(MEANX,MEANY,IN_IMAGE,SIZE,SIZE,
    1           SUMROW,MEANXROW,MEANYROW)

C           COMPUTE CENTRAL MOMENTS OF WEIGHTED IMAGE
            CALL FIND_CENTRAL_MOMENTS(MU,MAXORDER,IN_IMAGE,SIZE,SIZE,
    1           MEANX,MEANY,SCALE,MUROW)

C           COMPUTE ANGLE FROM SECOND MOMENTS
            IF (MU(1,1).NE.0.0 .OR. MU(2,0)-MU(0,2).NE.0.0) THEN
                    ANGLE = 90 - 0.5*ATAN2(2*MU(1,1), MU(2,0)-MU(0,2))*
    1                   (180.0/3.14159)
            ELSE
                    ANGLE = 0.0
            END IF

ANGLE = AMOD(ANGLE,180.0)
            IF (MU(3,0).LT.0) THEN
```

```
                ANGLE = ANGLE - 180
        END IF
        TRACE = (MU(2,0) + MU(0,2))/MU(0,0)
        AREA = (MU(2,0)*MU(0,2) - MU(1,1)**2)**.5/MU(0,0)

DO 55 P=0,MAXORDER
        DO 60 Q=0,(MAXORDER-P)
                GAMMA = (P+Q)/2.0
                ETA(P,Q) = MU(P,Q)/(MU(0,0)*TRACE**GAMMA)
60      CONTINUE
55      CONTINUE
        PHI(1) = ETA(2,0)+ETA(0,2)
        PHI(2) = SQRT((ETA(2,0)-ETA(0,2))**2 + 4*ETA(1,1)**2)
        PHI(3) = SQRT((ETA(3,0)-3*ETA(1,2))**2 +
     1          (3*ETA(2,1)-ETA(0,3))**2)
        PHI(4) = SQRT((ETA(3,0)+ETA(1,2))**2 + (ETA(2,1) + ETA(0,3))**2)
        PHI(5) = (ETA(3,0)-3*ETA(1,2))*(ETA(3,0)+ETA(1,2))*
     1          ((ETA(3,0)+ETA(1,2))**2 - 3*(ETA(2,1)+ETA(0,3))**2) +
     2          (3*ETA(2,1)-ETA(0,3))*(ETA(2,1)+ETA(0,3))*
     3          (3*(ETA(3,0)+ETA(1,2))**2 - (ETA(2,1)+ETA(0,3))**2)
        PHI(5) = SGN(PHI(5))*(ABS(PHI(5)))**0.25
        PHI(6) = (ETA(2,0)-ETA(0,2))*
     1          ((ETA(3,0)+ETA(1,2))**2-(ETA(2,1)+ETA(0,3))**2) +
     2       4*ETA(1,1)*(ETA(3,0)+ETA(1,2))*(ETA(2,1)+ETA(0,3))
        PHI(6) = SGN(PHI(6))*(ABS(PHI(6)))**0.33333
        PHI(7) = (3*ETA(2,1)-ETA(0,3))*(ETA(3,0)+ETA(1,2))*
     1          ((ETA(3,0)+ETA(1,2))**2 - 3*(ETA(2,1)+ETA(0,3))**2) +
     2       (3*ETA(1,2)-ETA(3,0))*(ETA(2,1)+ETA(0,3))*
     3          (3*(ETA(3,0)+ETA(1,2))**2 - (ETA(2,1)+ETA(0,3))**2)
        PHI(7) = SGN(PHI(7))*(ABS(PHI(7))**0.25)
        PHI(8) = SQRT((ETA(4,0)-6*ETA(2,2)+ETA(0,4))**2 +
     1       16*(ETA(1,3)-ETA(3,1))**2)
        PHI(9) = SQRT((ETA(4,0)-ETA(0,4))**2 +
     1          4*(ETA(3,1)+ETA(1,3))**2)
        PHI(10) = ETA(4,0) + 2*ETA(2,2) + ETA(0,4)
        PHI(11) = (ETA(4,0)-ETA(0,4))*(ETA(2,0)-ETA(0,2)) +
     1               4*ETA(1,1)*(ETA(3,1)+ETA(1,3))
        PHI(11) = SGN(PHI(11))*(ABS(PHI(11)))**0.5
        PHI(12) = 2*(ETA(4,0)-6*ETA(2,2)+ETA(0,4))*
     1          ((ETA(2,0)-ETA(0,2))**2 -
     1          4*ETA(1,1)**2) -
     1          32*ETA(1,1)*(ETA(1,3)-ETA(3,1))*(ETA(2,0)-ETA(0,2))
        PHI(12) = SGN(PHI(12))*(ABS(PHI(12)))**0.333333
        INVAR(0,0) = ETA(0,0)
        INVAR(1,0) = ETA(1,0)+I*ETA(0,1)
        INVAR(2,0) = ETA(2,0) - ETA(0,2) - 2*I*ETA(1,1)
        INVAR(1,1) = ETA(2,0) + ETA(0,2)
        INVAR(3,0) = ETA(3,0) - 3*ETA(1,2) + I*(ETA(0,3)-3*ETA(2,1))
        INVAR(2,1) = (ETA(3,0) + ETA(1,2)) - I*(ETA(2,1)+ETA(0,3))
        INVAR(4,0) = (ETA(4,0) - 6*ETA(2,2) + ETA(0,4)) +
     1          4*I*(ETA(1,3) - ETA(3,1))
        INVAR(3,1) = (ETA(4,0) - ETA(0,4)) - 2*I*(ETA(3,1)+ETA(1,3))
        INVAR(2,2) = ETA(4,0) + ETA(0,4) + 2*ETA(2,2)
C       SINCE PHI(1) IS ALWAYS 1, USE PHI(1) FOR THE ENTROPIC WIDTH
        PHI(1) = ENTROPIC_WIDTH/(WAVELENGTH*FNUM)
        RETURN
        END
```

```fortran
      REAL FUNCTION SGN(X)
C     IMPLICIT NONE
      REAL X
      IF (X.LT.0.0) THEN
            SGN = 1
      ELSE
            SGN = -1
      END IF
      RETURN
      END REAL FUNCTION PHASE(C)
C     IMPLICIT NONE
      REAL PI
      PARAMETER (PI=3.14159)
      COMPLEX C
      IF (ABS(C).GT.0.5E-2) THEN
            PHASE = 180*ATAN2(AIMAG(C),REAL(C))/PI
      ELSE
            PHASE = 0
      END IF
      END

SUBROUTINE VOLUME_ONE(IN_IMAGE,NROW,NCOL)
C     IMPLICIT NONE

INTEGER MAXCOL
      PARAMETER (MAXCOL=512)
      INTEGER NROW,NCOL
      REAL IN_IMAGE(NROW,NCOL)

INTEGER ROW,COL
      DOUBLE PRECISION SUM,SUM_COL

SUM = 0
      DO 55 COL=1,NCOL
      SUM_COL = 0
      DO 50 ROW=1,NROW
            SUM_COL = SUM_COL + IN_IMAGE(ROW,COL)
50    CONTINUE
      SUM = SUM_COL + SUM
55    CONTINUE

DO 75 COL=1,NCOL
      DO 70 ROW=1,NROW
            IN_IMAGE(ROW,COL) = IN_IMAGE(ROW,COL)/SUM
70    CONTINUE
75    CONTINUE
      RETURN
      END

SUBROUTINE ENTROPIC_LENGTH(LENGTH,IN_IMAGE,NROW,NCOL)
C     IMPLICIT NONE
```

```fortran
        INTEGER NROW,NCOL,ROW,COL
        DOUBLE PRECISION ENTROPY,ENTROPY_COL
        REAL LENGTH,IN_IMAGE(NROW,NCOL),TEMP ENTROPY = 0
        DO 55 COL=1,NCOL
              ENTROPY_COL = 0
              DO 50 ROW=1,NROW
                    IF (IN_IMAGE(ROW,COL) .EQ. 0.0) THEN
                          TEMP = 0
                    ELSE
                          TEMP =
     1                    IN_IMAGE(ROW,COL)*ALOG(IN_IMAGE(ROW,COL))
                    END IF
                    ENTROPY_COL = ENTROPY_COL - TEMP
50            CONTINUE
              ENTROPY = ENTROPY_COL + ENTROPY
55      CONTINUE
C       PRINT *, 'ENTROPY = ',ENTROPY
C       PRINT *, 'EXP(ENTROPY) = ',EXP(ENTROPY)
        LENGTH = SQRT(EXP(ENTROPY))
C       PRINT *, 'LENGTH = ',LENGTH
        RETURN
        END SUBROUTINE WEIGHT_IMAGE(IN_IMAGE,NROW,NCOL,MEANX,MEANY,DISTANCE)
C       IMPLICIT NONE C       INPUT ARGUMENTS
        INTEGER NROW,NCOL
        DOUBLE PRECISION MEANX,MEANY
        REAL DISTANCE

C       INPUT/OUTPUT ARGUMENTS
        REAL IN_IMAGE(NROW,NCOL)

C       LOCAL VARIABLES
        REAL WEIGHT_FACTOR
        INTEGER ROW,COL
        REAL SQ_DISTANCE

SQ_DISTANCE = DISTANCE**2
        DO 55 ROW=1,NROW
        DO 50 COL=1,NCOL
              WEIGHT_FACTOR =
     1              ((ROW-MEANY)**2+(COL-MEANX)**2)/SQ_DISTANCE
              IF (WEIGHT_FACTOR.LE.30.0) THEN
                    IN_IMAGE(ROW,COL) = EXP(-WEIGHT_FACTOR)*
     1                    IN_IMAGE(ROW,COL)
              ELSE
                    IN_IMAGE(ROW,COL) = 0
              END IF
50      CONTINUE
55      CONTINUE
        RETURN
        END
```

```
        SUBROUTINE FIND_MEANS(MEANX,MEANY,IN_IMAGE,NROW,NCOL,
     1      SUMROW,MEANXROW,MEANYROW)
C       IMPLICIT NONE

C       INPUT ARGUMENTS
        INTEGER NROW,NCOL
        REAL IN_IMAGE(NROW,NCOL)

C       OUTPUT ARGUMENTS
        DOUBLE PRECISION SUM,MEANX,MEANY
        DOUBLE PRECISION SUMROW(NROW),MEANXROW(NROW),MEANYROW(NROW)

C       LOCAL VARIABLES
        INTEGER ROW,COL

SUM = 0
        MEANX = 0
        MEANY = 0
        DO 55 ROW=1,NROW
        SUMROW(ROW) = 0
        MEANXROW(ROW)=0
        MEANYROW(ROW)=0
        DO 50 COL=1,NCOL
             SUMROW(ROW) = SUMROW(ROW) + IN_IMAGE(ROW,COL)
             MEANXROW(ROW) = MEANXROW(ROW) + COL*IN_IMAGE(ROW,COL)
             MEANYROW(ROW) = MEANYROW(ROW) + ROW*IN_IMAGE(ROW,COL)
50      CONTINUE
        SUM = SUMROW(ROW)+SUM
        MEANX = MEANXROW(ROW)+MEANX
        MEANY = MEANYROW(ROW)+MEANY
55      CONTINUE
        MEANX = MEANX/SUM
        MEANY = MEANY/SUM
        RETURN
        END

SUBROUTINE FIND_CENTRAL_MOMENTS(MU,MAXORDER,
     1      IN_IMAGE,NROW,NCOL,MEANX,MEANY,SCALE,MUROW)
C       IMPLICIT NONE

C       IN ARGUMENTS:
        INTEGER NROW,NCOL,MAXORDER
        REAL IN_IMAGE(NROW,NCOL)
        DOUBLE PRECISION MEANX,MEANY
        REAL SCALE

C       OUTPUT ARGUMENTS
        DOUBLE PRECISION MU(0:MAXORDER,0:MAXORDER),
     1      MUROW(0:MAXORDER,0:MAXORDER,NROW)

C       LOCAL VARIABLES
        INTEGER ROW,COL,P,Q

DO 55 P=0,MAXORDER
        DO 50 Q=0,MAXORDER-P
             MU(P,Q) = 0
50      CONTINUE
55      CONTINUE
```

```
            DO 100 ROW = 1,NROW
            DO 65 P=0,MAXORDER
            DO 60 Q=0,MAXORDER-P
                MUROW(P,Q,ROW) = 0
60      CONTINUE
65      CONTINUE
            DO 80 COL = 1,NCOL
                DO 75 P=0,MAXORDER
                DO 70 Q=0,MAXORDER-P
                    IF ((P.NE.0).AND.(Q.NE.0))
1                       THEN
                        MUROW(P,Q,ROW) = MUROW(P,Q,ROW) +
1                           ((COL-MEANX)**P)*((ROW-MEANY)**Q)*
2                           IN_IMAGE(ROW,COL)
                    ELSE IF ((P.EQ.0).AND.(Q.NE.0)) THEN
                        MUROW(P,Q,ROW) = MUROW(P,Q,ROW) +
1                           (ROW-MEANY)**Q*
2                           IN_IMAGE(ROW,COL)
                    ELSE IF ((P.NE.0).AND.(Q.EQ.0)) THEN
                        MUROW(P,Q,ROW) = MUROW(P,Q,ROW) +
1                           (COL-MEANX)**P*
2                           IN_IMAGE(ROW,COL)
                    ELSE
                        MUROW(P,Q,ROW) = MUROW(P,Q,ROW) +
                            IN_IMAGE(ROW,COL)
1                   END IF
70              CONTINUE
75              CONTINUE
80      CONTINUE
            DO 90 P=0,MAXORDER
            DO 85 Q=0,MAXORDER-P
                MU(P,Q) = MUROW(P,Q,ROW) + MU(P,Q)
85      CONTINUE
90      CONTINUE
100     CONTINUE

DO 110 P=0,MAXORDER
            DO 105 Q=0,MAXORDER-P
                MU(P,Q) = MU(P,Q)*SCALE**(P+Q)
105     CONTINUE
110     CONTINUE

RETURN
        END
```

Results

When trained against eight mixture cases with random defocus (standard deviation of 1/20 wave) and small amounts of other aberrations, the method of the present invention correctly classified 294 of 296 cases.

What is claimed is:

1. A method to be employed in conjunction with a radiation system, the radiation system comprising:
   (a) at least one source of radiation;
   (b) at least one imaging device for imaging at least a portion of the radiation emitted by the or each source onto at least one image plane;
   the or each imaging device functioning to produce at the image plane an intensity distribution profile; and
   (c) a detector array for recording the intensity distribution profile at the image plane;
   the method comprising the steps of:
   (1) defining a feature vector derived from the intensity distribution profile; and
   (2) employing an adaptive computational architecture for mapping the feature vector to at least one identifying characteristic of a selected imaging device.

2. A method according to claim 1, comprising deriving the feature vector from a point spread function produced by a point source of radiation.

3. A method according to claim 1, wherein the intensity distribution profile is recorded from an extended source for deriving the feature vector comprising power spectral components.

4. A method according to claim 1, comprising deriving the feature vector from a multi-dimensional moment vector.

5. A method according to claim 4, wherein the moment vector is defined by the equation $$M_{pq} = \int\int x^p y^q \rho_n(x,y) dx dy$$

where, $\rho_n(x,y)$ = a point spread function;

$x^p y^q$ is a weighting factor for each moment;

p,q are a pair of order variables for determining a particular moment; and x,y are a pair of position variables with respect to the point spread function.

6. A method according to claim 1, comprising learning steps of deriving the feature vector by:
   (a) inserting into the radiation system a set of n different imaging devices, each imaging device having known aberrations, for yielding n unique point spread functions; and
   (b) developing a multi-dimensional moment vector for each of the n unique point spread functions.

7. A method according to claim 1, comprising deriving the feature vector from an energy spectra.

8. A method according to claim 1, wherein the step of employing the adaptive computational architecture comprises:
   (a) providing a preliminary learning mode; and
   (b) providing a subsequent real-time processing mode.

9. A method according to claim 8, comprising providing a non-linear neural network computational architecture.

10. A method according to claim 9, wherein the learning mode comprises the steps of:
    iteratively adjusting a set of weighting factors defined by the neural network, by associating a succesion of known feature vectors with a succession of known aberrations.

11. A method according to claim 10, wherein the real time processing mode comprises the step of:
    characterizing a heretofore arbitrary feature vector, by processing the arbitrary feature vector through the neural network, the characterizing, at least in part, based on the learning mode.

12. A method according to claim 8, wherein the adaptive computational architecture comprises providing a statistical learning algorithm.

13. A method according to claim 12, comprising the learning mode steps of:
    (a) locating a known feature vector in a multi-dimensional feature vector space, the vector space corresponding to terms of orthogonal basis vectors; and
    (b) developing a region in the vector space, the region defined by the known feature vector and statistical noise components.

14. A method according to claim 13, comprising the real-time processing mode step of:
    characterizing a heretofore arbitrary feature vector by determining its location with respect to the region.

15. A radiation system comprising:
    (a) at least one source of radiation;
    (b) at least one imaging device for imaging at least a portion of the radiation emitted by the or each source onto at least one image plane;
    the or each imaging device functioning to produce at the image plane an intensity distribution profile;
    (c) a detector array for recording the intensity distribution profile at the image plane;
    (d) means for defining a feature vector derived from the intensity distribution profile; and
    (e) means for mapping the feature vector to at least one identifying characteristic of a selected imaging device.

16. A radiation system according to claim 15, wherein the source of radiation comprises a single point source emitting monochromatic radiation.

17. A radiation system according to claim 15, wherein the imaging device comprises a mirror.

18. A radiation system according to claim 15, wherein the imaging device comprises a lens.

19. A radiation system according to claim 15, wherein the detector array realizes a point spread function.

20. A radiation system according to claim 15, wherein the means for defining a feature vector comprises a means for deriving a moment analysis of a point spread function.

21. A radiation system according to claim 15, wherein the means for associating the feature vector with at least one identifying characteristic of a selected imaging device comprises a neural network, the neural network comprising:
    (a) a plurality of column input nodes, for inputting a column feature vector;
    (b) a plurality of non-linear column hidden nodes, each of which nodes inputs adjustable, weighted input signals $w_{ij}$ from each of the input nodes;
    (c) a plurality of column output nodes, each of which nodes accepts adjustable weighted input signals $w_{kl}$ from each of the hidden nodes; and
    (d) a plurality of column target nodes that are mated to the column output nodes.

22. A radiation system according to claim 21, wherein each of the non-linear column hidden nodes comprises:
    means for operating on the nodes inputs in accordance with a pair of equations (1) and (2):

$$B_i = f(\Sigma w_{ij} z_j) \quad (1)$$

$$f(x) = 1/(1 + \exp(-x)) \quad (2)$$

where, $w_{ij}$ = a set of weighted signals;

$z_j$ = contents of an input node number j;

$x = \Sigma w_{ij} z_j$; and $f(x)$ = a non-linear discriminator.

23. A radiation system according to claim 21, wherein the neural network comprises:
    (a) means for operating in a preliminary learning mode by iteratively adjusting the set of weighting signals $w_{ij}$ and $w_{kl}$, in response to associating a succession of known feature vectors with a succession of known imaging devices; and
    (b) means for operating in a subsequent real-time processing mode by processing an arbitrary feature vector through the neural network, and characterizing the arbitrary feature vector, at least in part, based on the learning mode.

* * * * *